United States Patent
Xiong

(10) Patent No.: US 11,879,159 B2
(45) Date of Patent: Jan. 23, 2024

(54) COMPOSITION AND REAGENT KIT FOR EARLY DETECTION OF CERVICAL HIGH-GRADE LESIONS AND CERVICAL CANCER

(71) Applicant: BEIJING ORIGIN-POLY BIO-TEC CO., LTD., Beijing (CN)

(72) Inventor: Sijun Xiong, Beijing (CN)

(73) Assignee: BEIJING ORIGIN-POLY BIO-TEC CO., LTD, Beijing (CN)

( * ) Notice: Subject to any disclaimer, the term of this patent is extended or adjusted under 35 U.S.C. 154(b) by 0 days.

(21) Appl. No.: 18/045,711

(22) Filed: Oct. 11, 2022

(65) Prior Publication Data

US 2023/0220488 A1    Jul. 13, 2023

Related U.S. Application Data

(63) Continuation of application No. PCT/CN2021/115485, filed on Aug. 31, 2021.

(51) Int. Cl.
*C12Q 1/6886*    (2018.01)
*C12Q 1/6848*    (2018.01)

(52) U.S. Cl.
CPC ......... *C12Q 1/6886* (2013.01); *C12Q 1/6848* (2013.01); *C12Q 2600/154* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS 7,820,386 B2    10/2010    Lai

FOREIGN PATENT DOCUMENTS

| CN | 105177164 | | 12/2015 |
|---|---|---|---|
| CN | 107287294 | A | 10/2017 |
| CN | 108085395 | A | 5/2018 |
| CN | 10578001 | | 12/2019 |
| CN | 110564857 | | 12/2019 |
| CN | 110578001 | A | 12/2019 |
| CN | 112048561 | | 12/2020 |
| WO | 2011036176 | A1 | 3/2011 |

*Primary Examiner* — Katherine D Salmon
(74) *Attorney, Agent, or Firm* — Nixon Peabody LLP; Mark J. FitzGerald

(57) ABSTRACT

The invention discloses a composition and kit for early detection of high-grade cervical lesions and cervical cancer, wherein the composition for early detection of high-grade cervical lesions and cervical cancer includes methylation primers, a probe corresponding to methylated sites and methylation blocking primers for FAM19A4 gene; methylation primers, a probe corresponding to methylated sites and methylation blocking primers for JAM3 gene; methylation primers, a probe corresponding to methylated sites and methylation blocking primers for PAX1 gene; and 1 pair of primers and a probe corresponding to methylated sites for internal reference gene GAPDH. The methylated sites in FAM19A4, JAM3 and PAX1 genes are accurately detected using multiple multi-channel fluorescence and blocking techniques through accurate recognition between specific primers and probes and methylated sequences, full release of methylated templates under the action of multiple blocking primers and optimized special methylation DNA polymerase.

10 Claims, 2 Drawing Sheets

Specification includes a Sequence Listing.

COMPOSITION AND REAGENT KIT FOR EARLY DETECTION OF CERVICAL HIGH-GRADE LESIONS AND CERVICAL CANCER

CROSS-REFERENCE TO RELATED APPLICATIONS

This application is a continuation of International Application No. PCT/CN2021/115485 filed on Aug. 31, 2021, which claims benefit under 35 U.S.C. § 119(b) of CN Application No. 202010986280.3 filed on Sep. 18, 2020, the contents of both which are incorporated herein by reference in their entireties.

TECHNICAL FIELD

The invention belongs to the technical field of nucleic acid in vitro diagnosis, and specifically relates to a composition and a kit for applying specific gene methylation markers to early detection of high-grade cervical lesions and cervical cancer.

SEQUENCE LISTING

The instant application contains a Sequence Listing which has been submitted in XML format via Patent Center and is hereby incorporated by reference in its entirety. Said XML copy, created on Oct. 10, 2022, is 070019-000100USC1_SL.xml and is 22,770 bytes in size.

BACKGROUND ART

At present, cervical cancer is the fourth most common type of cancer in women in the world. According to statistics, in 2018, there were 570,000 new cases of cervical cancer and 311,000 deaths worldwide. Cervical cancer has become the main cause of cancer deaths among women in most low- and middle-income countries. The cause of cervical cancer is clear, and persistent high-risk human papillomavirus (HPV) infection is a necessary condition. The progression from cervical precancerous lesions to invasive cervical cancer can take up to ten years, so early cervical cancer screening can be effectively block the progression of precancerous lesions. In recent years, the incidence of cervical cancer has younger trend. The incidence of women under the age of 35 has increased significantly, accounting for about 30% of new cases. Other data show that the incidence of cervical cancer is geographically different, and the incidence of rural residents is higher than that of urban residents, the incidence in central China is higher than that in the east and west. These differences may be partly attributed to the lack of effective screening and prevention measures for cervical cancer. In recent years, with the development of genetic testing and gene editing technologies, the promotion of preventive HPV vaccines, and the development and research of therapeutic vaccines, new directions have been pointed out for the early screening and prevention of cervical cancer.

Human papillomavirus (HPV) is considered to be the most important cause of cervical cancer. Its relationship with cervical cancer was first proposed by the German scientist Harald zur Hausen in the 1970s, and then was verified. According to research, HPV has more than 100 subtypes which currently are usually divided into low-risk and high-risk types according to their carcinogenicity: low-risk HPV usually does not cause malignant lesions, but high-risk HPV infection may eventually lead to cervical precancerous lesions and cervical cancer. For example, the two main high-risk HPV viruses, HPV-16 and HPV-18, are mostly related to more than 90% of cervical cancers. Under normal circumstances, the vast majority of HPV infections are temporary, and more than 90% of infections will be cleared within 2 to 3 years. This is believed to be due to human cellular regulatory immune system. However, it is worth noting that antibodies to HPV-16 virus after infection seem to only have a relatively ordinary effect, and patients who fail to clean HPV-16 spontaneously have the risk of developing into CIN (cervical intraepithelial neoplasia) and even cervical cancer in the following years or decades.

Early screening is an effective method to prevent cervical precancerous lesions and cervical cancer. At present, the commonly used clinical detection methods mainly include liquid-based cytological detection and HPV detection. Compared with the traditional Pap smear method (the sensitivity is between 30% and 87%, and sometimes the sensitivity is even lower than 20%), the liquid-based cytological detection has a certain improvement, but there is still a certain percentage of false negative results (studies have shown that the probability of false negatives is about 50%). Since persistent high-risk HPV infection is the primary cause of cervical lesions, the detection of HPV nucleotides has extremely high sensitivity (about 90% in the literature data) in the detection of cervical lesions, but because only a small part of the patients with high-risk HPV infection will show cervical lesions, so HPV detection shows very low specificity (approximately 60.7%), especially in young women.

DNA methylation is a modification mode of epigenetics. Research reports that DNA methylation can affect the gene expression and silence of normal mammalian cells; at the same time, it has been found in human tumor research that DNA methylation usually leads to changes of CpG island in the promoter region of a tumor suppressor gene. Hypermethylation or hypomethylation in the promoter region of a tumor suppressor gene may lead to cell transformation, making the DNA methylation status a potential marker for tumor detection.

DNA methylation mainly occurs in the promoter region (where DNA begins to be transcribed into RNA) of a gene, and is usually closely related to the inactivation of the expression of a tumor suppressor gene. Common methods used in methylation research are: methylation-specific PCR (MSP), bisulfite sequencing PCR (BSP) and high resolution melting (HRM) etc. Methylation-specific PCR mainly relies on the binding of primers with target templates for PCR amplification to detect methylated sites; the bisulfite sequencing PCR relies on sequencing primers for PCR amplification, and subsequent sequencing is performed on this basis to realize the detection of methylated sites; the high-resolution melting distinguishes between methylated and non-methylated status mainly through the change of the melting temperature caused by the change of the CG content in the sample. Each method has its own characteristics. The BSP has high accuracy and is easy for intuitive interpretation, but has low sensitivity, relatively more cumbersome operation, and high cost; the HRM method has relatively low sensitivity, and has slightly complicated analysis for the results; the PCR has high detection sensitivity and relatively low requirements for samples, at the same time, has short detection time, has low cost, and has results easy to interpret.

Cervical exfoliated cells are currently the main source of samples for cervical cancer screening. Whether it is liquid-based cytological detection or HPV detection, collecting the secretions of cervical exfoliated cells is a necessary operation. The remaining cell preservation solution can be used in this kit for methylation studies, and in terms of sample source, it would not cause additional inconvenience to patients. For a kit for detecting gene methylation status, high sensitivity and high specificity are very important indicators. On one aspect, it is because the normal gene background is relatively high, and on another aspect, it is because of the high loss caused by the limitation of the current transformation technology in the experimental process.

At present, there are many phenomena of non-specific amplification (false positive results) in PCR amplification. At present, the most mainstream bisulfite conversion technology performs conversion on the extracted samples. Limited by the limitations of current bisulfite conversion technology, in addition to about 80% of the target genome may be lost, there would also be a certain probability of unconverted templates. These are the reasons that may cause false positive results.

In view of this, the present invention is proposed.

SUMMARY OF THE INVENTION

The purpose of the present invention is to provide a composition and kit for early detection of high-grade cervical lesions and cervical cancer to solve the problem of false positive results being prone to occur in routine detection.

In order to achieve the above purpose, the present invention provides a composition for early detection of high-grade cervical lesions and cervical cancer, which includes FAM19A4 gene methylation primers, JAM3 gene methylation primers and PAX1 gene methylation primers and 1 pair of primers for internal reference gene GAPDH, the sequences of the primers are as follows:

```
FAM19A4 gene methylation forward primer F:
ATTTCGGTTAAAACGGTGAAATTTC,

FAM19A4 gene methylation reverse primer R:
TACAAACTCCGCCTCCCG;

JAM3 gene methylation forward primer F:
ATAGGGTAGCGGCGGTTG,

JAM3 gene methylation reverse primer R:
ACGACAACGACGACGACAC;

PAX1 gene methylation forward primer F:
TCGTGTTCGGGATTTCG,

PAX1 gene methylation reverse primer R:
AAACAAATAAACAACCGCCGT;

Internal reference gene GAPDH forward
primer F:
TTATTTTTTGGTATGTGGTTGG,

Internal reference gene GAPDH reverse
primer R:
ACCACCCTATTACTATAACCAAATT.
```

A composition for early detection of high-grade cervical lesions and cervical cancer (cervical cancer and cervical lesions of different grades are diverse. The combined detection of the methylated regions in multiple genes is functionally complementary to each other, is beneficial to improve the detection rate of high-grade lesions and cervical cancer and is used as an auxiliary early diagnosis of high-grade lesions and cervical cancer) includes FAM19A4 gene methylation-specific primer, JAM3 gene methylation-specific primer and PAX1 gene methylation-specific primer and 1 pair of primers for internal reference gene.

For the design of methylation-specific primers, mainly, multiple CpG islands are distributed on the forward and reverse primers and it is best to distribute 2-3 CG sites in each primer to improve the specificity and accuracy of the primers to recognize methylated regions and increase detection sensitivity and specificity.

Further, the composition further includes the Taqman probe corresponding to methylated sites in FAM19A4 gene, the Taqman probe corresponding to methylated sites in JAM3 gene, the Taqman probe corresponding to methylated sites in PAX1 gene, and the Taqman probe corresponding to the internal reference gene GAPDH, and the sequences of the probes are as follows:

```
FAM19A4 gene probe:
FAM-TTAGTCGGGCGTAGTGGCGCGCGTTT-BHQ1;

JAM3 gene probe:
ROX-ATTCGTGGAGACGCGTCGTCGTTA-BHQ2;

PAX1 gene probe:
CY5-TTGGCGTTCGTGGGCGATACGGGATT-BHQ2;

Internal reference gene GAPDH probe:
VIC-TTTGGTGGTTGGTTTAGAAAAAGGGTTTTGA-BHQ1
```

The detection system uses a single tube to detect the four genes, and the four genes need to be reflected in the form of Ct values through different fluorescence channels. Therefore, the amplification of each of the four genes in the system does not interfere with each other, and the amplification efficiency of each of the four genes is consistent with the corresponding single amplification efficiency. This shows that the multiple reaction system is not affected by inhibition. Therefore, a large number of primers were designed and screened to determine the above specific sequences. Through the combined detection of three target genes FAM19A4, JAM3 and PAX1 and reasonable threshold setting, the accuracy of early detection of cervical cancer is increased. The invention uses a special primer design method and clinical samples with accurate pathological information to determine a reasonable positive judgment value through the ROC curve. The accuracy of screening in the reaction system and the reliability of early detection of high-grade cervical lesions and cervical cancer are improved. The occurrence of false positive and false negative results is minimized. And the detection performance of the entire kit is significantly improved.

Further specific recognition of methylated regions is achieved through subsequent probe design, that is, the probes can distinguish whether FAM19A4, JAM3 and PAX1 genes are methylated. The key points for the probe design are: the probes specifically distinguish between methylated and unmethylated regions; the difference $\Delta G$ between the free energy of binding of the probe with the methylated template and the free energy of binding of the probe with the unmethylated template is 20 kcal mol$^{-1}$; since the sequence after bisulfite conversion has only three bases, A, T, and G (except for the CG site), primers or probes are very easy to interfere with each other and affect each other in terms of amplification, and these need to be avoided during designing; the composition for early detection of high-grade cervical lesions and cervical cancer further includes the Taqman probe corresponding to methylated sites in FAM19A4 gene, the Taqman probe corresponding to methylated sites in JAM3 gene, the Taqman probe corresponding to methylated sites in PAX1 gene, and the Taqman probe corresponding to the internal reference gene; in addition to 4 pairs of methylation-specific amplification primers, 4 probes labeled with different fluorescent channels are added to this reaction system; the main point of screening is to observe whether the amplification efficiency of 4 genes in standard samples with different methylation degrees is the best, whether the fluorescence curve is a standard S-shaped amplification curve, and whether the fluorescence curve maintains a consistent trend compared with the single amplification of each gene.

The sequences of the four probes are respectively composed of four-channel fluorescence FAM, ROX, CY5 and VIC. Using the design technique that the difference ΔG between the free energy of binding of the probe with the methylated template and the free energy of binding of the probe with the unmethylated template is 20 kcal mol−1, the binding efficiency of the probe and the methylated template is significantly improved, this is more conducive to the recognition of methylated sites and the specificity and sensitivity of detection are further improved.

Further, the composition further includes FAM19A4 gene methylation blocking primers, JAM3 gene methylation blocking primers and PAX1 gene methylation blocking primers and the sequences of the blocking primers are as follows:

```
FAM19A4 gene methylation blocking primer 1:
GCCGGGCGTAGTGGCGCGCG-C3 spacer;

FAM19A4 gene methylation blocking primer 2:
AGTTGGGTGTAGTGGTGTGTGT-C3 spacer;

JAM3 gene methylation blocking primer 1:
CTCGTGGAGACGCGCCGCC-C3 spacer;

JAM3 gene methylation blocking primer 2:
TTGTGGAGATGTGTTGTTGTT-C3 spacer;

PAX1 gene methylation blocking primer 1:
GCGCCCGTGGGCGACACGGG-C3 spacer;

PAX1 gene methylation blocking primer 2:
TGGTGTTTGTGGGTGATATGG-C3 spacer.
```

There are multiple template sequences in the conversion product of genomic DNA, such as unconverted genomic DNA, genomic DNA that is methylated in the region containing methylation sites after conversion, genomic DNA that is not methylated in the region containing methylation sites after conversion, etc. Therefore, the composition of the converted product after bisulfite conversion is more complicated, and relying only on specific primers and probes is susceptible to interference from other sequence templates, and cannot well recognize the methylated region of the corresponding gene. In order to fully release the sequence template with the methylated region in the converted product so that specific primers and probes can better recognize and bind, special blocking primer design technique is introduced and the key points of the blocking primer design are that: blocking primers can block unconverted sequence templates; blocking primers can block sequence templates that are not methylated in the methylated region after conversion. This design method simplifies the originally complicated converted product, and a variety of sequences that interfere with the target template sequences are blocked, so that the genomic DNA that is methylated in the region containing methylation sites is more exposed, the added specific primers and probes can better bind to the target templates and the sensitivity and specificity for the detection of methylated region are greatly improved. The composition used for early detection of high-grade cervical lesions and cervical cancer further includes corresponding blocking primers for each gene in the case where no conversion occurs and corresponding blocking primers for each gene in the case where the methylated region is not methylated after conversion. In addition to 4 pairs of methylation-specific primers and 4 multi-channel fluorescently labeled probes, 6 specific blocking primers are added to this reaction system. The key points of the screening are that: the blocking primers and the primers and the probes do not affect each other and do not interfere with the amplification efficiency; the addition of the blocking primers enhances the sensitivity and specificity of detection.

Preferably, for one detection, FAM19A4 gene forward primer F at 100 μmol/L is added in an amount of 0.10-0.50 μL, FAM19A4 gene reverse primer R at 100 μmol/L is added in an amount of 0.10-0.50 μL, JAM3 gene forward primer F at 100 μmol/L is added in an amount of 0.10-0.50 μL, JAM3 gene reverse primer R at 100 μmol/L is added in an amount of 0.10-0.50 μL, PAX1 gene forward primer F at 100 μmol/L is added in an amount of 0.10-0.50 μL, PAX1 gene reverse primer R at 100 μmol/L is added in an amount of 0.10-0.50 μL, internal reference gene GAPDH forward primer F at 100 μmol/L is added in an amount of 0.01-0.50 μL, and internal reference gene GAPDH reverse primer R at 100 μmol/L is added in an amount of 0.01-0.50 μL.

Preferably, for one detection, FAM19A4 gene probe at 100 μmol/L is added in an amount of 0.05-0.50 μL, JAM3 gene probe at 100 μmol/L is added in an amount of 0.05-0.50 μL, PAX1 gene probe at 100 μmol/L is added in an amount of 0.05-0.50 μL, and internal reference gene GAPDH probe at 100 μmon is added in an amount of 0.01-0.10 μL.

Preferably, for one detection, FAM19A4 gene blocking primer 1 at 100 μmol/L is added in an amount of 0.50-1.00 μL, FAM19A4 gene blocking primer 2 at 100 μmol/L is added in an amount of 0.50-1.00 μL, JAM3 gene blocking primer 1 at 100 μmol/L is added in an amount of 0.50-1.00 μL, JAM3 gene blocking primer 2 at 100 μmol/L is added in an amount of 0.50-1.00 μL, PAX1 gene blocking primer 1 at 100 μmol/L is added in an amount of 0.50-1.00 μL, and PAX1 gene blocking primer 2 at 100 μmol/L is added in an amount of 0.50-1.00 μL.

The present invention also provides a kit for early detection of high-grade cervical lesions and cervical cancer, including the above-mentioned composition for early detection of high-grade cervical lesions and cervical cancer.

Further, the kit further includes a positive quality control and a negative quality control.

Further, the kit further includes a PCR reaction solution, the PCR reaction solution includes a Taq DNA polymerase, dNTPs, $Mg^{2+}$ and a 10×DNA polymerase buffer.

For the detection of methylated sites, special DNA polymerases related to methylation detection are required, and polymerases with better amplification efficiency are screened. In this reaction system containing multiple primers and probes, the choice of PCR reaction solution is particularly important. The amplification efficiency of each gene primer and probe in the system should be similar to that of its corresponding single amplification to ensure that the primers or probes in the system do not interfere with each other, and give full play to the amplification effect of each set of primers and probes.

Preferably, for one detection, Taq DNA polymerase at 1 U/μL is added in an amount of 0.3-0.8 μL, dNTPs at 25 mmol/L are added in an amount of 2.0-4.0 μL, $Mg^{2+}$ at 1.5 mmol/L is added in an amount of 3.0-5.0 μL, and 10×DNA polymerase buffer is added in an amount of 4.0-6.0 μL.

The screening of Taq DNA polymerase and the ratio of Taq DNA polymerase to dNTPs, $Mg^{2+}$ and 10×DNA polymerase buffer in the system is directly related to the amplification efficiency of the combination of the primers and the probes.

The composition and kit for early detection of high-grade cervical lesions and cervical cancer provided by the present invention have the following beneficial effects:

1. Detection of methylated sites in FAM19A4, JAM3 and PAX1 genes in the present invention includes not only the promoter regions of the genes, but also the coding regions of the genes. Due to the diversity of high-grade cervical lesions and cervical cancer types and the diversity of HPV infections, the combined detection of methylated regions of multiple genes which are complementary between functions is selected to significantly improve the sensitivity of the detection of cervical cancer and high-grade cervical lesions, but has high specificity for normal and low-grade cervical lesions. The kit detects patients with possible cervical cancer and high-grade cervical lesions early through molecular epigenetic methods using methylation detection technology for early preventive treatment.

2. The methylated sites in FAM19A4, JAM3 and PAX1 genes are accurately detected mainly using multiple multi-channel fluorescence and bocking techniques through accurate recognition between specific primers and probes and methylated sequences, full release of methylated templates under the action of multiple blocking primers and optimized special methylation DNA polymerase. Compared with the detection method using only PCR specific primers, dual recognition of methylated sites can be performed with the additional use of specific probes at the same time to significantly improve the sensitivity and accuracy of detection. And the technology using multiple blocking primers is introduced. The present invention uses this technology to perform multiple multi-channel fluorescence methylation detection in multiple genes. The test samples involved are easy to obtain. The detection method is simple to operate and intuitive to interpret, and results can be obtained within 8 hours. Universal fluorescence quantitative PCR instrument can meet the detection needs. The entire experimental process adopts a one-stop fully enclosed form, which avoids the possibility of cross-contamination. Due to the high detection sensitivity of the present invention, the present invention has better detection efficiency for low-concentration templates. The combined ROC curve area of the three genes FAM19A4, JAM3 and PAX1 is 0.900. The high detection sensitivity of this kit is suitable for triaging high-grade cervical lesions. The overall specificity is 93.1%, and the overall sensitivity is 83.9%. Wherein, the detection rates for CIN2, CIN3, cervical squamous cell carcinoma and cervical adenocarcinoma are 61.54%, 84.21%, 100% and 88.89%, respectively and the negative detection rates for CIN1 and inflammation were 94.1% and 92.5%, respectively. From the above results, it can be seen that this kit can better identify high-grade cervical lesions and cancer, so as to realize triage from low-grade lesions and inflammation, and reduce unnecessary colposcopy referrals to a certain extent.

DETAILED DESCRIPTION OF EMBODIMENTS

Figure 1:
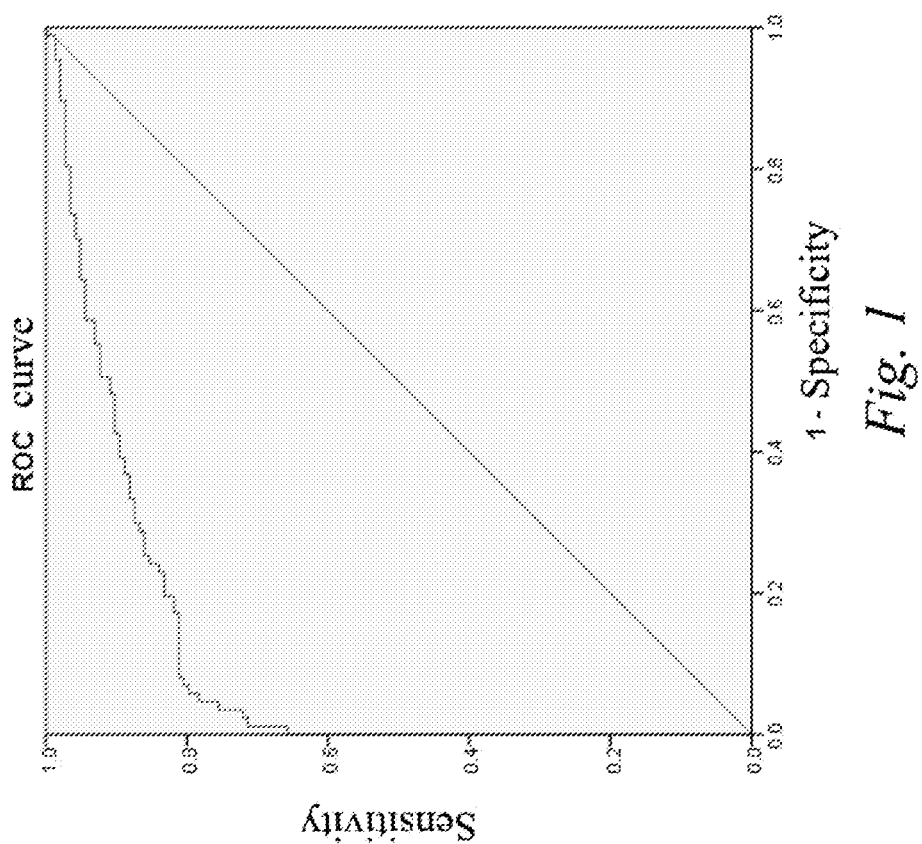
FIG. 1 is a graph of the ROC curve obtained from 230 samples detected by the kit used for early detection of cervical high-grade lesions and cervical cancer in the specific embodiments.
Figure 2:
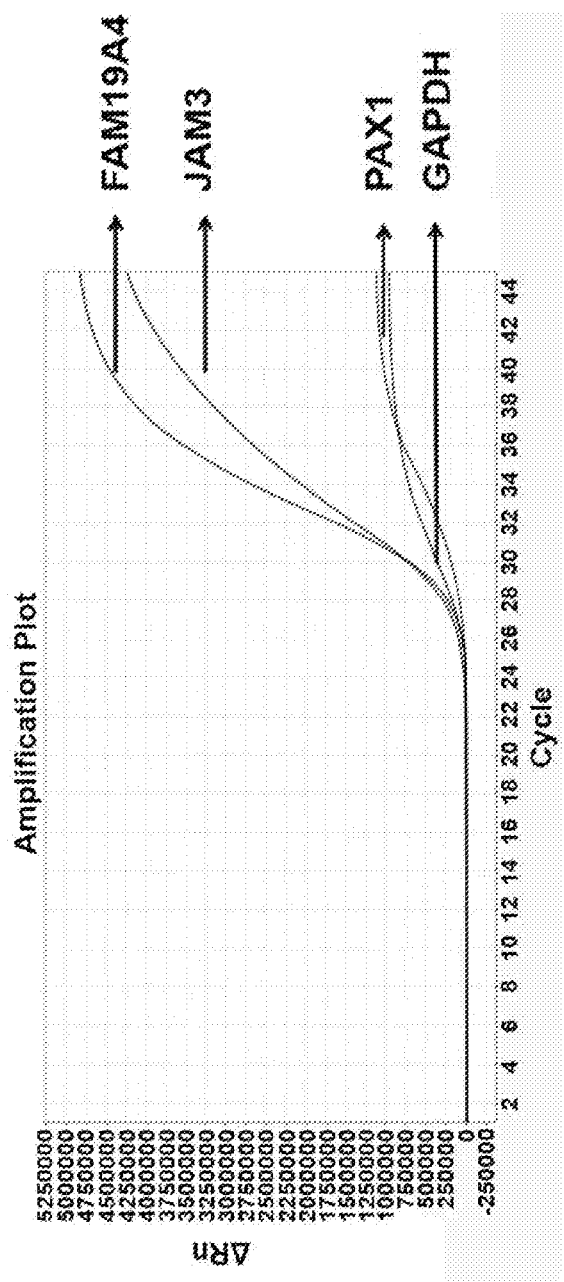
FIG. 2 is a graph of S-shaped amplification curves of FAM19A4, JAM3 and PAX1 genes and internal reference gene (GAPDH) in the specific embodiments.

In order to enable those skilled in the art to better understand the solutions of the present invention, the present invention will be further described in detail below with reference to the specific implementations.

This patent involves three markers related to cervical cancer:

FAM19A4 (family with sequence similarity 19 member A4) gene, which is a member of the TAFA gene family; the TAFA gene family mainly encodes small molecular proteins which are related to stress and inflammation. FAM19A4 is the ligand of formyl peptide receptor 1 and can promote phagocytosis and increase the reactive oxygen species released by macrophages. FAM19A4 is usually up-regulated in monocytes and macrophages stimulated by lipopolysaccharide. In recent years, some research reports have shown that FAM19A4 is closely related to cervical cancer, is an important cervical cancer marker and is also an important triage method for high-risk patients with HPV infection in cervical cancer screening.

JAM3 (junctional adhesion molecule 3) is a member of the JAM gene family. The JAM gene family can directly affect the tight junction between epithelial cells and endothelial cells. A large number of documents and studies report that JAM3, commonly referred to as JAMC, is a regulator for the junction. In recent years, many documents report that JAM3 has an important role in regulating tumors during tumor development, such as its methylation is manifested both in colorectal cancer and cervical cancer.

The PAX1 (paired box gene 1) gene is a member of the PAX gene family located on chromosome 20 and plays a key role in fetal development and cell proliferation. The methylation in the PAX1 gene promoter plays an important epigenetic regulatory role in the occurrence and development of tumors. Studies show that PAX1 is methylated and silenced in cervical cancer and ovarian cancer, so PAX1 is also regarded as a tumor suppressor gene.

Cervical exfoliated cells are currently the main source of samples for cervical cancer screening. Whether it is liquid-based cytological detection or HPV detection, collecting the secretions of cervical exfoliated cells is a necessary operation. The remaining cell preservation solution can be used in this kit for methylation studies, and in terms of sample source, it would not cause additional inconvenience to patients. For a kit for detecting gene methylation status, high sensitivity and high specificity are very important indicators. On one aspect, it is because the normal gene background is relatively high, and on another aspect, it is because of the high loss caused by the limitation of the current transformation technology in the experimental process.

The composition and kit for early detection of high-grade cervical lesions and cervical cancer detect the methylated sites in the regions in the genes closely related to the development of cervical cancer in the exfoliated cells in cervical secretions, and the genes include FAM19A4 gene, JAM3 gene and PAX1 gene. The methylated sites in the above three genes that are closely related to the occurrence of cervical cancer are detected. The highly methylated CpG island regions in FAM19A4, JAM3 and PAX1 genes are selected. And the detection of multiple methylated regions in multiple genes is realized by reaction in a single tube. The present invention utilizes the technology of introducing blocking primers in the methylation detection to fully release the methylated sequences, and not only the detection sensitivity is improved, but also the detection specificity is improved.

A composition for early detection of high-grade cervical lesions and cervical cancer (cervical cancer and cervical lesions of different grades are diverse. The combined detection of the methylated regions in multiple genes is functionally complementary to each other, is beneficial to improve the detection rate of high-grade lesions and cervical cancer and is used as an auxiliary early diagnosis of high-grade lesions and cervical cancer) includes FAM19A4 gene methylation-specific primer, JAM3 gene methylation-specific primer and PAX1 gene methylation-specific primer and 1 pair of primers for internal reference gene. The specific primer sequences are as follows:

```
FAM19A4 gene forward primer F:
ATTTCGGTTAAAACGGTGAAATTTC,

FAM19A4 gene reverse primer R:
TACAAACTCCGCCTCCCG;

JAM3 gene forward primer F:
ATAGGGTAGCGGCGGTTG,

JAM3 gene reverse primer R:
ACGACAACGACGACGACAC;

PAX1 gene forward primer F:
TCGTGTTCGGGATTTCG,

PAX1 gene reverse primer R:
AAACAAATAAACAACCGCCGT.

Internal reference gene (GAPDH)
forward primer F:
TTATTTTTTGGTATGTGGTTGG,

Internal reference gene (GAPDH)
reverse primer R:
ACCACCCTATTACTATAACCAAATT.
```

For the design of methylation-specific primers, mainly, multiple CpG islands are distributed on the forward and reverse primers and it is best to distribute 2-3 CG sites in each primer to improve the specificity and accuracy of the primers to recognize methylated regions and increase detection sensitivity and specificity. The detection system uses a single tube to detect the four genes, and the four genes need to be reflected in the form of Ct values through different fluorescence channels. Therefore, the amplification of each of the four genes in the system does not interfere with each other, and the amplification efficiency of each of the four genes is consistent with the corresponding single amplification efficiency. This shows that the multiple reaction system is not affected by inhibition. Therefore, a large number of primers were designed and screened to determine the above specific sequences. Through the combined detection of three target genes FAM19A4, JAM3 and PAX1 and reasonable threshold setting, the accuracy of early detection of cervical cancer is increased. The invention uses a special primer design method and clinical samples with accurate pathological information to determine a reasonable positive judgment value through the ROC curve. The accuracy of screening in the reaction system and the reliability of early detection of high-grade cervical lesions and cervical cancer are improved. The occurrence of false positive and false negative results is minimized. And the detection performance of the entire kit is significantly improved.

Further specific recognition of methylated regions is achieved through subsequent probe design, that is, the probes can distinguish whether FAM19A4, JAM3 and PAX1 genes are methylated. The key points for the probe design are: the probes specifically distinguish between methylated and unmethylated regions; the difference ΔG between the free energy of binding of the probe with the methylated template and the free energy of binding of the probe with the unmethylated template is 20 kcal mol$^{-1}$; since the sequence after bisulfite conversion has only three bases, A, T, and G (except for the CG site), primers or probes are very easy to interfere with each other and affect each other in terms of amplification, and these need to be avoided during designing; the composition for early detection of high-grade cervical lesions and cervical cancer further includes the Taqman probe corresponding to methylated sites in FAM19A4 gene, the Taqman probe corresponding to methylated sites in JAM3 gene, the Taqman probe corresponding to methylated sites in PAX1 gene, and the Taqman probe corresponding to the internal reference gene; in addition to 4 pairs of methylation-specific amplification primers, 4 probes labeled with different fluorescent channels are added to this reaction system; the main point of screening is to observe whether the amplification efficiency of 4 genes in standard samples with different methylation degrees is the best, whether the fluorescence curve is a standard S-shaped amplification curve, and whether the fluorescence curve maintains a consistent trend compared with the single amplification of each gene. After a large number of designs and screenings, the specific nucleotide sequences of the four probes are determined as follows:

```
FAM19A4 gene probe:
FAM-TTAGTCGGGCGTAGTGGCGCGCGTTT-BHQ1;

JAM3 gene probe:
ROX-ATTCGTGGAGACGCGTCGTCGTTA-BHQ2;

PAX1 gene probe:
CY5-TTGGCGTTCGTGGGCGATACGGGATT-BHQ2;

Internal reference gene (GAPDH) probe:
VIC-TTTGGTGGTTGGTTTAGAAAAAGGGTTTTGA-BHQ1.
```

The sequences of the four probes are respectively composed of four-channel fluorescence FAM, ROX, CY5 and VIC. Using the design technique that the difference ΔG between the free energy of binding of the probe with the methylated template and the free energy of binding of the probe with the unmethylated template is 20 kcal mol-1, the binding efficiency of the probe and the methylated template is significantly improved, this is more conducive to the recognition of methylated sites and the specificity and sensitivity of detection are further improved.

There are multiple template sequences in the conversion product of genomic DNA, such as unconverted genomic DNA, genomic DNA that is methylated in the region containing methylation sites after conversion, genomic DNA that is not methylated in the region containing methylation sites after conversion, etc. Therefore, the composition of the converted product after bisulfite conversion is more complicated, and relying only on specific primers and probes is susceptible to interference from other sequence templates, and cannot well recognize the methylated region of the corresponding gene. In order to fully release the sequence template with the methylated region in the converted product so that specific primers and probes can better recognize and bind, special blocking primer design technique is introduced in the present invention and the key points of the blocking primer design are that: blocking primers can block unconverted sequence templates; blocking primers can block sequence templates that are not methylated in the methylated region after conversion. This design method simplifies the originally complicated converted product, and a variety of sequences that interfere with the target template sequences are blocked, so that the genomic DNA that is methylated in the region containing methylation sites is more exposed, the added specific primers and probes can better bind to the target templates and the sensitivity and specificity for the detection of methylated region are greatly improved. The composition used for early detection of high-grade cervical lesions and cervical cancer further includes corresponding blocking primers for each gene in the case where no conversion occurs and corresponding blocking primers for each gene in the case where the methylated region is not methylated after conversion. In addition to 4 pairs of methylation-specific primers and 4 multi-channel fluorescently labeled probes, 6 specific blocking primers are added to this reaction system. The key points of the screening are that: the blocking primers and the primers and the probes do not affect each other and do not interfere with the amplification efficiency; the addition of the blocking primers enhances the sensitivity and specificity of detection; through a large number of designs and screenings, the specific nucleotide sequences are as follows:

```
FAM19A4 gene blocking primer 1:
GCCGGGCGTAGTGGCGCGCG-C3 spacer;

FAM19A4 gene blocking primer 2:
AGTTGGGTGTAGTGGTGTGTGT-C3 spacer;

JAM3 gene blocking primer 1:
CTCGTGGAGACGCGCCGCC-C3 spacer;

JAM3 gene blocking primer 2:
TTGTGGAGATGTGTTGTTGTT-C3 spacer;

PAX1 gene blocking primer 1:
GCGCCCGTGGGCGACACGGG-C3 spacer;

PAX1 gene blocking primer 2:
TGGTGTTTGTGGGTGATATGG-C3 spacer.
```

To use PCR fluorescent probe method to realize the detection of gene methylation, one of the most important points is to achieve as much as possible the enrichment and capture of the fragments where the target methylated sites are located. The extracted sample contains not only the target methylated genomes, but also a large number of genomes unmethylated at the same site; this is an important factor leading to non-specific amplification (giving false positive results) in subsequent PCR amplification. On another aspect, at present, the most mainstream bisulfite conversion technology is used to perform conversion on the extracted samples. Limited by the limitations of current bisulfite conversion technology, in addition to about 80% of the target genomes may be lost, there would also be a certain probability of unconverted templates. And this is another possible cause of false positive results in PCR amplification. Therefore, as far as possible, the templates that are not methylated and the templates that are not converted are consumed or blocked so that the target converted methylated templates are actually enriched to a certain extent, exposed to the matched primer environment and are captured successfully to achieve fluorescence excitation and collection. Therefore, during the development of this kit, blocking primers that have different effects on these three genes were added to realize the blocking of other sequences that may cause non-specific amplification so that target sequences were enriched to complete the detection of the methylation status of these three genes with the kit.

In addition to the combination of primers and probes, the kit used for early detection of high-grade cervical lesions and cervical cancer requires a corresponding methylation-specific PCR reaction solution. Because the present invention is to detect methylated sites, special DNA polymerases related to methylation detection are required, and polymerases with better amplification efficiency are screened. In this reaction system containing multiple primers and probes, the choice of PCR reaction solution is particularly important. The amplification efficiency of each gene primer and probe in the system should be similar to that of its corresponding single amplification to ensure that the primers or probes in the system do not interfere with each other, and give full play to the amplification effect of each set of primers and probes. The PCR reaction solution includes DNA Taq polymerase, dNTPs, $Mg^{2+}$, 10×DNA polymerase buffer, etc. The screening of DNA polymerase and the ratio of DNA polymerase to dNTPs, $Mg^{2+}$ and 10×DNA polymerase buffer in the system is directly related to the amplification efficiency of the combination of the primers and the probes. The components in the kit are shown in Table 1.

TABLE 1

The components in the kit

| Components | Main ingredients |
| --- | --- |
| PCR reaction solution | Taq DNA polymerase, dNTPs, $Mg^{2+}$, 10 × DNA polymerase buffer, etc. |
| Mixed solution of primers and probes | FAM19A4 gene forward and reverse primers, probes and blocking primers 1 and 2, JAM3 gene forward and reverse primers, probes and blocking primers 1 and 2, PAX1 gene forward and reverse primers, probes and blocking primers 1 and 2, internal reference gene primers and probes |
| Positive quality control | Cell line genomic DNA fragment |
| Negative quality control | Cell line genomic DNA fragment |

The formulation of the PCR reaction solution in the amplification reaction system is shown in Table 2.

TABLE 2

The component list of the PCR reaction solution (25 ul/person)

| Components | Adding amount/person (μL) |
| --- | --- |
| Taq DNA polymerase (1 U/μL) | 0.5 |
| dNTPs (25 mM) | 3 |
| $Mg^{2+}$ (1.5 mM) | 4 |
| 10 × DNA polymerase buffer | 5 |
| Purified water | Make up to 25 μL |

The formulation of the mixed solution of primers and probes is shown in Table 3.

TABLE 3

The component list of the mixed solution of primers (20 μL/person)

| Components | Adding amount/person (μL) |
| --- | --- |
| FAM19A4 gene-F (100 μM) | 0.2 |
| FAM19A4 gene-R (100 μM) | 0.2 |
| FAM19A4 gene-FP (100 μM) | 0.1 |

TABLE 3-continued

The component list of the mixed solution of primers (20 µL/person)

| Components | Adding amount/person (µL) |
|---|---|
| JAM3 gene-F (100 µM) | 0.25 |
| JAM3 gene-R (100 µM) | 0.25 |
| JAM3 gene-FP (100 µM) | 0.15 |
| PAX1 gene-F (100 µM) | 0.3 |
| PAX1 gene-R (100 µM) | 0.2 |
| PAX1 gene-FP (100 µM) | 0.15 |
| FAM19A4 gene blocking primer 1 (100 µM) | 0.85 |
| FAM19A4 gene blocking primer 2 (100 µM) | 0.8 |
| JAM3 gene blocking primer 1 (100 µM) | 0.75 |
| JAM3 gene blocking primer 2 (100 µM) | 0.6 |
| PAX1 gene blocking primer 1 (100 µM) | 0.6 |
| PAX1 gene blocking primer 2 (100 µM) | 0.7 |
| Internal reference gene-F (100 µM) | 0.05 |
| Internal reference gene-R (100 µM) | 0.05 |
| Internal reference gene-FP (100 µM) | 0.05 |
| Purified water | Make up to 20 µL |

A detection test using the kit for early detection of high-grade cervical lesions and cervical cancer utilizes the ingredients of the above-mentioned composition and kit for early detection of high-grade cervical lesions and cervical cancer and includes the following steps:

(1) Sample source: 230 cervical exfoliated cell samples with known and clear pathological information from women who are not younger than 21 years old were selected: 41 samples were identified as cervical adenocarcinoma and squamous cell carcinoma samples; 34 samples were samples of low-grade intraepithelial lesions (CIN1); 102 samples were samples of high-grade intraepithelial lesions (CIN2 and CIN3); 53 samples were samples of inflammation.

(2) Cell genomic DNA extraction was performed on the above 230 cervical exfoliated cell samples, and a blood/cell/tissue genomic DNA extraction kit was used to extract genomic DNA from the above samples. In this example, the blood/cell/tissue genomic DNA extraction kit (DP304) of Tiangen Biotech (Beijing) Co., Ltd. was selected for the extraction.

During the extraction process, it is necessary to ensure the quality of the extracted DNA for subsequent tests. The quality of DNA after extraction was monitored, and the OD260/280 is between 1.8 and 2.0.

(3) The cell genomic DNA obtained in step (2) was subjected to bisulfite conversion, the total amount for conversion is 100 ng-1000 ng, and even the genomic DNA template with a total amount as low as 50 ng can be detected. The unmethylated 5' cytosine (C) in the DNA was converted into uracil (U), while the methylated 5' cytosine (C) remained unchanged, and finally the converted Bis-DNA was obtained. In this example, the DNA Bisulfite Conversion Kit (DP215) of Tiangen Biotech (Beijing) Co., Ltd. was selected and the DNA conversion efficiency and the final Bis-DNA conversion yield must be ensured during the conversion process.

(4) The PCR reaction solution and the mixed solution of primers and probes were formulated according to Table 2 and Table 3. Different formulation ratios and reaction conditions were closely related to the final PCR amplification efficiency, and constant screening and comparison were required and the best conditions were selected. The specific preferences are as follows: the PCR mixture includes the templates before conversion with a total amount of 100 ng-1000 ng, primers at 100-300 nM, probes at 100-300 nM, blocking primers at 400-1200 nM, Taq DNA polymerase at 1 U/µL, MgCl$_2$ at 1-5 mM, dNTPs at 20-30 mM, and 10×DNA polymerase buffer.

(5) Samples were added, as shown in Table 1, 5 µL of each of the positive quality control and the converted Bis-DNA clinical sample as the negative quality control was added to the mixed solution system formulated in step (4).

(6) The optimal PCR reaction conditions were screened: pre-denaturation at 96° C. for 5 min; denaturation at 94° C. for 15 s, annealing and extension at 60° C. for 35 s, 45 cycles; keep at 25° C. for 10 min. PCR amplification was performed using the Bis-DNA obtained in step (3) as a template. Signals were collected, and FAM, VIC, ROX and CY5 signals were collected at 60° C.

(7) Analysis of detection results

By selecting clinical samples with clear pathological information, the positive judgment value of the reaction system in the kit for methylation detection was determined by ROC curve. Cervical cancer (adenocarcinoma, squamous cell carcinoma, etc.) samples, low-grade cervical lesion samples (CIN1), high-grade cervical lesion samples (CIN2 and CIN3), and inflammation samples were included. That is, if at least one gene of the detected FAM19A4, JAM3 and PAX1 genes was methylated, the risk of occurrence of cervical cancer was high.

A total of 230 samples were detected using the reaction system in the above kit, including 41 cervical cancer samples, 34 low-grade intraepithelial lesions (CIN1) samples, 102 high-grade intraepithelial lesions (CIN2 and CIN3) samples, and 53 inflammation samples. The detection results are shown in Table 4. Comparing the clinicopathological results, the combined ROC curve area of the three genes obtained using this kit for methylation detection was 0.900 (as shown in FIG. 1). The overall specificity was 93.1%, and the overall sensitivity was 83.9%. The detection rates for CIN2, CIN3, cervical squamous cell carcinoma and cervical adenocarcinoma were 61.54%, 84.21%, 100% and 88.89%, respectively and the negative detection rates for CIN1 and inflammation were 94.1% and 92.5%, respectively. From the above results, it can be seen that this kit can better identify high-grade cervical lesions and cervical cancer, so as to realize triage from low-grade lesions and inflammation, and reduce unnecessary colposcopy referrals to a certain extent.

TABLE 4

Detection results of a total of 230 samples detected by the reaction system in the kit

| Sample number | Pathology | Methylation results |
|---|---|---|
| 1 | Squamous cell carcinoma | Positive |
| 2 | Squamous cell carcinoma | Positive |
| 3 | Squamous cell carcinoma | Positive |
| 4 | CIN3 | Positive |
| 5 | Squamous cell carcinoma | Positive |
| 6 | Squamous cell carcinoma | Positive |
| 7 | Squamous cell carcinoma | Positive |
| 8 | Squamous cell carcinoma | Positive |
| 9 | CIN3 | Positive |
| 10 | Squamous cell carcinoma | Positive |
| 11 | Squamous cell carcinoma | Positive |
| 12 | CIN3 | Positive |
| 13 | Squamous cell carcinoma | Positive |
| 14 | CIN3 | Positive |
| 15 | Squamous cell carcinoma | Positive |
| 16 | Squamous cell carcinoma | Positive |
| 17 | CIN3 | Positive |
| 18 | Squamous cell carcinoma | Positive |
| 19 | CIN3 | Positive |
| 20 | CIN3 | Positive |
| 21 | Squamous cell carcinoma | Positive |
| 22 | Squamous cell carcinoma | Positive |

TABLE 4-continued

Detection results of a total of 230 samples detected by the reaction system in the kit

| Sample number | Pathology | Methylation results |
| --- | --- | --- |
| 23 | Squamous cell carcinoma | Positive |
| 24 | CIN3 | Positive |
| 25 | Squamous cell carcinoma | Positive |
| 26 | Squamous cell carcinoma | Positive |
| 27 | Squamous cell carcinoma | Positive |
| 28 | Adenocarcinoma | Positive |
| 29 | CIN3 | Positive |
| 30 | Squamous cell carcinoma | Positive |
| 31 | Squamous cell carcinoma | Positive |
| 32 | Squamous cell carcinoma | Positive |
| 33 | CIN3 | Positive |
| 34 | Squamous cell carcinoma | Positive |
| 35 | Adenocarcinoma | Positive |
| 36 | CIN3 | Positive |
| 37 | CIN3 | Positive |
| 38 | Squamous cell carcinoma | Positive |
| 39 | CIN3 | Positive |
| 40 | Squamous cell carcinoma | Positive |
| 41 | CIN3 | Positive |
| 42 | CIN3 | Positive |
| 43 | CIN3 | Positive |
| 44 | CIN3 | Positive |
| 45 | CIN3 | Positive |
| 46 | CIN2 | Positive |
| 47 | CIN3 | Positive |
| 48 | Squamous cell carcinoma | Positive |
| 49 | CIN3 | Positive |
| 50 | CIN3 | Positive |
| 51 | Adenocarcinoma | Positive |
| 52 | CIN3 | Positive |
| 53 | Squamous cell carcinoma | Positive |
| 54 | CIN3 | Positive |
| 55 | CIN3 | Positive |
| 56 | CIN3 | Positive |
| 57 | Squamous cell carcinoma | Positive |
| 58 | CIN3 | Positive |
| 59 | CIN2 | Positive |
| 60 | CIN3 | Positive |
| 61 | CIN3 | Positive |
| 62 | CIN2 | Positive |
| 63 | CIN3 | Positive |
| 64 | CIN3 | Positive |
| 65 | CIN3 | Positive |
| 66 | CIN3 | Positive |
| 67 | Adenocarcinoma | Positive |
| 68 | Squamous cell carcinoma | Positive |
| 69 | Squamous cell carcinoma | Positive |
| 70 | Adenocarcinoma | Positive |
| 71 | Inflammation | Positive |
| 72 | CIN3 | Positive |
| 73 | CIN3 | Positive |
| 74 | CIN3 | Positive |
| 75 | CIN3 | Positive |
| 76 | CIN3 | Positive |
| 77 | CIN2 | Positive |
| 78 | CIN3 | Positive |
| 79 | CIN2 | Positive |
| 80 | CIN3 | Positive |
| 81 | CIN3 | Positive |
| 82 | CIN3 | Positive |
| 83 | CIN3 | Positive |
| 84 | CIN3 | Positive |
| 85 | CIN3 | Positive |
| 86 | CIN3 | Positive |
| 87 | CIN3 | Positive |
| 88 | Squamous cell carcinoma | Positive |
| 89 | CIN3 | Positive |
| 90 | CIN2 | Positive |
| 91 | CIN3 | Positive |
| 92 | Adenocarcinoma | Positive |
| 93 | CIN2 | Positive |
| 94 | Adenocarcinoma | Positive |
| 95 | CIN3 | Positive |
| 96 | Squamous cell carcinoma | Positive |
| 97 | Adenocarcinoma | Positive |
| 98 | CIN3 | Positive |
| 99 | CIN1 | Positive |
| 100 | Inflammation | Positive |
| 101 | CIN3 | Positive |
| 102 | CIN3 | Positive |
| 103 | CIN2 | Positive |
| 104 | CIN1 | Positive |
| 105 | CIN2 | Positive |
| 106 | CIN3 | Positive |
| 107 | CIN2 | Positive |
| 108 | CIN3 | Positive |
| 109 | CIN3 | Positive |
| 110 | CIN3 | Positive |
| 111 | Inflammation | Positive |
| 112 | CIN3 | Positive |
| 113 | CIN2 | Negative |
| 114 | CIN1 | Negative |
| 115 | CIN2 | Positive |
| 116 | CIN2 | Positive |
| 117 | CIN3 | Positive |
| 118 | CIN3 | Positive |
| 119 | CIN3 | Negative |
| 120 | CIN2 | Negative |
| 121 | CIN3 | Positive |
| 122 | Inflammation | Negative |
| 123 | CIN2 | Positive |
| 124 | CIN2 | Positive |
| 125 | CIN3 | Negative |
| 126 | CIN3 | Negative |
| 127 | Inflammation | Negative |
| 128 | Inflammation | Positive |
| 129 | Inflammation | Negative |
| 130 | Inflammation | Negative |
| 131 | Inflammation | Negative |
| 132 | Inflammation | Negative |
| 133 | CIN2 | Positive |
| 134 | Inflammation | Negative |
| 135 | CIN1 | Negative |
| 136 | CIN1 | Negative |
| 137 | Inflammation | Negative |
| 138 | Inflammation | Negative |
| 139 | Inflammation | Negative |
| 140 | Inflammation | Negative |
| 141 | CIN2 | Positive |
| 142 | CIN3 | Positive |
| 143 | Inflammation | Negative |
| 144 | CIN3 | Negative |
| 145 | CIN1 | Negative |
| 146 | Inflammation | Negative |
| 147 | CIN3 | Positive |
| 148 | CIN1 | Negative |
| 149 | CIN1 | Negative |
| 150 | CIN1 | Negative |
| 151 | CIN1 | Negative |
| 152 | CIN1 | Negative |
| 153 | CIN1 | Negative |
| 154 | CIN1 | Negative |
| 155 | CIN1 | Negative |
| 156 | Inflammation | Negative |
| 157 | Inflammation | Negative |
| 158 | Inflammation | Negative |
| 159 | CIN1 | Negative |
| 160 | Inflammation | Negative |
| 161 | Inflammation | Negative |
| 162 | Inflammation | Negative |
| 163 | Inflammation | Negative |
| 164 | CIN1 | Negative |
| 165 | CIN2 | Negative |
| 166 | Inflammation | Negative |
| 167 | CIN1 | Negative |
| 168 | CIN3 | Positive |
| 169 | CIN1 | Negative |
| 170 | Inflammation | Negative |
| 171 | CIN1 | Negative |
| 172 | CIN3 | Negative |

TABLE 4-continued

Detection results of a total of 230 samples detected by the reaction system in the kit

| Sample number | Pathology | Methylation results |
|---|---|---|
| 173 | Inflammation | Negative |
| 174 | Inflammation | Negative |
| 175 | CIN3 | Positive |
| 176 | CIN1 | Negative |
| 177 | Inflammation | Negative |
| 178 | CIN2 | Negative |
| 179 | CIN3 | Negative |
| 180 | CIN1 | Negative |
| 181 | CIN3 | Negative |
| 182 | CIN1 | Negative |
| 183 | Inflammation | Negative |
| 184 | Inflammation | Negative |
| 185 | Inflammation | Negative |
| 186 | Inflammation | Negative |
| 187 | Inflammation | Negative |
| 188 | Adenocarcinoma | Negative |
| 189 | Inflammation | Negative |
| 190 | CIN1 | Negative |
| 191 | CIN2 | Negative |
| 192 | Inflammation | Negative |
| 193 | CIN1 | Negative |
| 194 | CIN3 | Negative |
| 195 | CIN1 | Negative |
| 196 | Inflammation | Negative |
| 197 | CIN3 | Negative |
| 198 | Inflammation | Negative |
| 199 | Inflammation | Negative |
| 200 | Inflammation | Negative |
| 201 | CIN1 | Negative |
| 202 | Inflammation | Negative |
| 203 | Inflammation | Negative |
| 204 | Inflammation | Negative |
| 205 | CIN2 | Negative |
| 206 | Inflammation | Negative |
| 207 | CIN1 | Negative |
| 208 | Inflammation | Negative |
| 209 | CIN1 | Negative |
| 210 | CIN1 | Negative |
| 211 | CIN1 | Negative |
| 212 | CIN3 | Negative |
| 213 | Inflammation | Negative |
| 214 | CIN1 | Negative |
| 215 | CIN3 | Negative |
| 216 | Inflammation | Negative |
| 217 | Inflammation | Negative |
| 218 | CIN2 | Negative |
| 219 | CIN1 | Negative |
| 220 | Inflammation | Negative |
| 221 | Inflammation | Negative |
| 222 | CIN1 | Negative |
| 223 | Inflammation | Negative |
| 224 | CIN2 | Negative |
| 225 | CIN2 | Negative |
| 226 | CIN3 | Negative |
| 227 | Inflammation | Negative |
| 228 | CIN1 | Negative |
| 229 | CIN2 | Negative |
| 230 | Inflammation | Negative |

(8) Interpretation and analysis of results a. If the followings were met, the result was judged as negative: the internal standard channel had an S-shaped amplification curve, and the Ct value was ≤33; PAX1, FAM19A4 and JAM3 gene channels all had no S-shaped amplification curve or the $\Delta$ Ct value for PAX1 gene >7.08 and the $\Delta$ Ct value for FAM19A4 gene >8.94 and the $\Delta$ Ct value for JAM3 gene >11.62;

b. If the followings were met, the result was judged as positive: the internal standard channel had an S-shaped amplification curve, and the Ct value was ≤33; the $\Delta$ Ct value for PAX1 gene detection ≤7.08, or the $\Delta$ Ct value for FAM19A4 gene detection ≤8.94, or the $\Delta$ Ct value for JAM3 gene ≤11.62; the channel detection of at least one of the three genes met the corresponding $\Delta$ Ct value requirements;

c. If there was no S-shaped amplification curve in the internal standard channel or the Ct value was >33, the result was judged as invalid, and re-extracting samples for detection was recommended.

Herein, specific examples are used to describe the inventive concept in detail, and the description of the above embodiments is only used to help understand the core idea of the present invention. It should be pointed out that for those of ordinary skill in the art, any obvious modification, equivalent replacement or other improvement made should be included in the protection scope of the present invention without departing from the inventive concept.

What is claimed is:

1. A composition for early detection of high-grade cervical lesions and cervical cancer, characterized in that: the composition includes FAM19A4 gene methylation primers, JAM3 gene methylation primers and PAX1 gene methylation primers and 1 pair of primers for internal reference gene GAPDH, wherein:

the sequence of the FAM19A4 gene methylation forward primer F is SEQ ID NO. 1, the sequence of the FAM19A4 gene methylation reverse primer R is SEQ ID NO. 2;

the sequence of the JAM3 gene methylation forward primer F is SEQ ID NO. 3, the sequence of the JAM3 gene methylation reverse primer R is SEQ ID NO. 4;

the sequence of the PAX1 gene methylation forward primer F is SEQ ID NO. 5, the sequence of the PAX1 gene methylation reverse primer R is SEQ ID NO. 6;

the sequence of the internal reference gene GAPDH forward primer F is SEQ ID NO. 7, and the sequence of the internal reference gene GAPDH reverse primer R is SEQ ID NO. 8.

2. The composition for early detection of high-grade cervical lesions and cervical cancer according to claim 1, characterized in that: the composition further includes the Taqman probe corresponding to methylated sites in FAM19A4 gene, the Taqman probe corresponding to methylated sites in JAM3 gene, the Taqman probe corresponding to methylated sites in PAX1 gene, and the Taqman probe corresponding to the internal reference gene GAPDH, wherein:

the sequence of the FAM19A4 gene probe is FAM-SEQ ID NO. 9-BHQ1;

the sequence of the JAM3 gene probe is ROX-SEQ ID NO. 10-BHQ2;

the sequence of the PAX1 gene probe is CY5-SEQ ID NO. 11-BHQ2; and the sequence of the internal reference gene GAPDH probe is VIC-SEQ ID NO. 12-BHQ1.

3. The composition for early detection of high-grade cervical lesions and cervical cancer according to claim 1, characterized in that: the composition further includes FAM19A4 gene methylation blocking primers, JAM3 gene methylation blocking primers and PAX1 gene methylation blocking primers, wherein:

the sequence of the FAM19A4 gene methylation blocking primer 1 is SEQ ID NO. 13 with a -C3 spacer at its 3' end;

the sequence of the FAM19A4 gene methylation blocking primer 2 is SEQ ID NO. 14 with a -C3 spacer at its 3' end;

the sequence of the JAM3 gene methylation blocking primer 1 is SEQ ID NO. 15 with a -C3spacer at its 3' end;

the sequence of the JAM3 gene methylation blocking primer 2 is SEQ ID NO. 16 with a -C3spacer at its 3' end;

the sequence of the PAX1 gene methylation blocking primer 1 is SEQ ID NO. 17 with a -C3spacer at its 3' end; and the sequence of the PAX1 gene methylation blocking primer 2 is SEQ ID NO. 18 with a -C3spacer at its 3' end.

4. The composition for early detection of high-grade cervical lesions and cervical cancer according to claim 1, characterized in that: for one detection, FAM19A4 gene forward primer F at 100 μmol/L is added in an amount of 0.10-0.50 μL, FAM19A4 gene reverse primer Rat 100 μmol/L is added in an amount of 0.10-0.50 μL, JAM3 gene forward primer F at 100 μmol/L is added in an amount of 0.10-0.50 μL, JAM3 gene reverse primer R at 100 μmol/L is added in an amount of 0.10-0.50 μL, PAX1 gene forward primer F at 100 μmol/L is added in an amount of 0.10-0.50 μL, PAX1 gene reverse primer R at 100 μmol/L is added in an amount of 0.10-0.50 μL, internal reference gene GAPDH forward primer F at 100 μmol/L is added in an amount of 0.01-0.50 μL, and internal reference gene GAPDH reverse primer R at 100 μmol/L is added in an amount of 0.01-0.50 μL.

5. The composition for early detection of high-grade cervical lesions and cervical cancer according to claim 2, characterized in that: for one detection, FAM19A4 gene probe at 100 μmol/L is added in an amount of 0.05-0.50 μL, JAM3 gene probe at 100 μmol/L is added in an amount of 0.05-0.50 μL, PAX1 gene probe at 100 μmol/L is added in an amount of 0.05-0.50 μL, and internal reference gene GAPDH probe at 100 μmol/L is added in an amount of 0.01-0.10 μL.

6. The composition for early detection of high-grade cervical lesions and cervical cancer according to claim 3, characterized in that: for one detection, FAM19A4 gene blocking primer 1 at 100 μmol/L is added in an amount of 0.50-1.00 μL, FAM19A4 gene blocking primer 2 at 100 μmol/L is added in an amount of 0.50-1.00 μL, JAM3 gene blocking primer 1 at 100 μmol/L is added in an amount of 0.50-1.00 μL, JAM3 gene blocking primer 2 at 100 μmol/L is added in an amount of 0.50-1.00 μL, PAX1 gene blocking primer 1 at 100 μmol/L is added in an amount of 0.50-1.00 μL, and PAX1 gene blocking primer 2 at 100 μmol/L is added in an amount of 0.50-1.00 μL.

7. A kit for early detection of high-grade cervical lesions and cervical cancer, characterized in that: the kit includes the composition for early detection of high-grade cervical lesions and cervical cancer according to claim 1.

8. The kit for early detection of high-grade cervical lesions and cervical cancer according to claim 7, characterized in that: the kit further includes a positive quality control and a negative quality control.

9. The kit for early detection of high-grade cervical lesions and cervical cancer according to claim 7, characterized in that: the kit further includes a PCR reaction solution, the PCR reaction solution includes a Taq DNA polymerase, dNTPs, $Mg^{2+}$ and a 10×DNA polymerase buffer.

10. The kit for early detection of high-grade cervical lesions and cervical cancer according to claim 9, characterized in that: for one detection, the Taq DNA polymerase at 1 U/μL is added in an amount of 0.3-0.8 μL, the dNTPs at 25 mmol/L are added in an amount of 2.0-4.0 μL, the $Mg^{2+}$ at 1.5 mmol/L is added in an amount of 3.0-5.0 μL, and the 10×DNA polymerase buffer is added in an amount of 4.0-6.0 μL.

* * * * *

SEQUENCE LISTING

```
Sequence total quantity: 18
SEQ ID NO: 1            moltype = DNA  length = 25
FEATURE                 Location/Qualifiers
source                  1..25
                        mol_type = other DNA
                        organism = synthetic construct
SEQUENCE: 1
atttcggtta aaacggtgaa atttc                                             25

SEQ ID NO: 2            moltype = DNA  length = 18
FEATURE                 Location/Qualifiers
source                  1..18
                        mol_type = other DNA
                        organism = synthetic construct
SEQUENCE: 2
tacaaactcc gcctcccg                                                     18

SEQ ID NO: 3            moltype = DNA  length = 18
FEATURE                 Location/Qualifiers
source                  1..18
                        mol_type = other DNA
                        organism = synthetic construct
```

```
SEQUENCE: 3
atagggtagc ggcggttg                                                  18

SEQ ID NO: 4              moltype = DNA   length = 19
FEATURE                   Location/Qualifiers
source                    1..19
                          mol_type = other DNA
                          organism = synthetic construct
SEQUENCE: 4
acgacaacga cgacgacac                                                 19

SEQ ID NO: 5              moltype = DNA   length = 17
FEATURE                   Location/Qualifiers
source                    1..17
                          mol_type = other DNA
                          organism = synthetic construct
SEQUENCE: 5
tcgtgttcgg gatttcg                                                   17

SEQ ID NO: 6              moltype = DNA   length = 21
FEATURE                   Location/Qualifiers
source                    1..21
                          mol_type = other DNA
                          organism = synthetic construct
SEQUENCE: 6
aaacaaataa acaaccgccg t                                              21

SEQ ID NO: 7              moltype = DNA   length = 22
FEATURE                   Location/Qualifiers
source                    1..22
                          mol_type = other DNA
                          organism = synthetic construct
SEQUENCE: 7
ttatttttg gtatgtggtt gg                                              22

SEQ ID NO: 8              moltype = DNA   length = 25
FEATURE                   Location/Qualifiers
source                    1..25
                          mol_type = other DNA
                          organism = synthetic construct
SEQUENCE: 8
accaccctat tactataacc aaatt                                          25

SEQ ID NO: 9              moltype = DNA   length = 26
FEATURE                   Location/Qualifiers
source                    1..26
                          mol_type = other DNA
                          organism = synthetic construct
misc_feature              1
                          note = The probe has FAM at the N-terminus of nucleotide 1
misc_feature              26
                          note = The probe has BHQ1 at the C-terminus of nucleotide 26
SEQUENCE: 9
ttagtcgggc gtagtggcgc gcgttt                                         26

SEQ ID NO: 10             moltype = DNA   length = 24
FEATURE                   Location/Qualifiers
source                    1..24
                          mol_type = other DNA
                          organism = synthetic construct
misc_feature              1
                          note = The probe has ROX at the N-terminus of nucleotide 1
misc_feature              24
                          note = The probe has BHQ2 at the C-terminus of nucleotide 24
SEQUENCE: 10
attcgtggag acgcgtcgtc gtta                                           24

SEQ ID NO: 11             moltype = DNA   length = 26
FEATURE                   Location/Qualifiers
source                    1..26
                          mol_type = other DNA
                          organism = synthetic construct
misc_feature              1
                          note = The probe has CY5 at the N-terminus of nucleotide 1
misc_feature              26
                          note = The probe has BHQ2 at the C-terminus of nucleotide 26
SEQUENCE: 11
ttggcgttcg tgggcgatac gggatt                                         26
```

```
SEQ ID NO: 12             moltype = DNA   length = 31
FEATURE                   Location/Qualifiers
source                    1..31
                          mol_type = other DNA
                          organism = synthetic construct
misc_feature              1
                          note = The probe has VIC at the N-terminus of nucleotide 1
misc_feature              30
                          note = The probe has BHQ1 at the C-terminus of nucleotide 30
SEQUENCE: 12
tttggtggtt ggtttagaaa aagggttttg a                                  31

SEQ ID NO: 13             moltype = DNA   length = 20
FEATURE                   Location/Qualifiers
source                    1..20
                          mol_type = other DNA
                          organism = synthetic construct
misc_feature              20
                          note = The primer has C3spacer at the C-terminus of
                           nucleotide 20
SEQUENCE: 13
gccgggcgta gtggcgcgcg                                               20

SEQ ID NO: 14             moltype = DNA   length = 22
FEATURE                   Location/Qualifiers
source                    1..22
                          mol_type = other DNA
                          organism = synthetic construct
misc_feature              22
                          note = The primer has C3spacer at the C-terminus of
                           nucleotide 22
SEQUENCE: 14
agttgggtgt agtggtgtgt gt                                            22

SEQ ID NO: 15             moltype = DNA   length = 19
FEATURE                   Location/Qualifiers
source                    1..19
                          mol_type = other DNA
                          organism = synthetic construct
misc_feature              19
                          note = The primer has C3spacer at the C-terminus of
                           nucleotide 19
SEQUENCE: 15
ctcgtggaga cgcgccgcc                                                19

SEQ ID NO: 16             moltype = DNA   length = 21
FEATURE                   Location/Qualifiers
source                    1..21
                          mol_type = other DNA
                          organism = synthetic construct
misc_feature              21
                          note = The primer has C3spacer at the C-terminus of
                           nucleotide 21
SEQUENCE: 16
ttgtggagat gtgttgttgt t                                             21

SEQ ID NO: 17             moltype = DNA   length = 20
FEATURE                   Location/Qualifiers
source                    1..20
                          mol_type = other DNA
                          organism = synthetic construct
misc_feature              20
                          note = The primer has C3spacer at the C-terminus of
                           nucleotide 20
SEQUENCE: 17
gcgcccgtgg gcgacacggg                                               20

SEQ ID NO: 18             moltype = DNA   length = 21
FEATURE                   Location/Qualifiers
source                    1..21
                          mol_type = other DNA
                          organism = synthetic construct
misc_feature              21
                          note = The primer has C3spacer at the C-terminus of
                           nucleotide 21
SEQUENCE: 18
tggtgtttgt gggtgatatg g                                             21
```